US00PP08392P

United States Patent [19]

Zaiger et al.

[11] Patent Number: Plant 8,392

[45] Date of Patent: Sep. 28, 1993

[54] APRICOT TREE "JORDANNE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 997,529

[22] Filed: Dec. 28, 1992

[51] Int. Cl.[5] ..... A01H 5/00

[52] U.S. Cl. ..... Plt./39

[58] Field of Search ..... Plt./39

[56] References Cited

U.S. PATENT DOCUMENTS

P.P. 5,138 11/1983 Zeiger ..... Plt. 39

*Primary Examiner*—James R. Feyrer

[57] ABSTRACT

The present new and distinct variety of apricot tree has the following unique combination of desirable features that are outstanding in a new variety:

1. Large size of fruit throughout the tree.
2. Early maturity of the fruit.
3. Fruit with good handling and shipping quality.
4. Heavy and regular bearing of fruit.
5. Vigorous and semi-spreading growth.
6. Fruit with good flavor and eating quality.
7. Fruit having high soluble solids (14.0 Brix) with a good balance between sugar and acid.

1 Drawing Sheet

ORIGIN OF THE VARIETY

The new and distinct variety of apricot tree was originated by us in the experimental orchard, located near Modesto, Calif. as a first generation cross between a selected seedling and King Cot Apricot (non-patented). The selected seedling used as the female parent originated from a cross between Flaming Gold Apricot (U.S. Plant Pat. No. 2,822) and Gold Kist Apricot (U.S. Plant Pat. No. 2,826). A large group of these first generation seedlings were planted and grown under careful observation by us: one such seedling, which is the present variety, having been especially desirable for its fruit quality and heavy production was selected for asexual reproduction and commercialization.

ASEXUAL REPRODUCTION OF THE VARIETY

Asexual reproduction of the new and distinct variety of apricot tree was performed by budding in our experimental orchard located near Modesto, Calif. and shows that all characteristics of the tree and its fruit run true to form and are established and transmitted in succeeding propagations.

SUMMARY OF THE VARIETY

The new and distinct variety of apricot tree is of large size, vigorous, semi-spreading in growth, and a regular and productive bearer of large, firm, yellow flesh, freestone fruit with good flavor and eating quality. The fruit is further characterized by its early maturity, the ability to ship to long distance markets and when compared to Flaming Gold Apricot (U.S. Plant Pat. No. 2,822), the new variety has more uniform large size fruit with greater production and matures approximately 12 days earlier.

BRIEF DESCRIPTION OF THE PHOTOGRAPHS

Typical specimens are shown in the accompanying photographs of the fruit and foliage of our new variety of apricot tree. The upper and lower surface of the leaves being illustrated, with an exterior view of the fruit and a fruit being divided on its suture plane to reveal flesh coloration, showing a stone remaining in place. The photographs were taken shortly after the fruit was picked at maturity (firm ripe) and the colors are as nearly true as is reasonably possible in a color representation of this type.

DESCRIPTION OF THE VARIETY

The following is a detailed botanical description of our new variety of apricot tree, its flowers, foliage and fruit as based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Growth.*—Semi-spreading.
- *Production.*—Productive.
- *Bearing.*—Regular.

Trunk:
- *Size.*—Stocky.
- *Surface.*—Medium shaggy.
- *Color.*—Grayish brown to brown (4-E-b 4) to (5-E-4).

Branches:
- *Size.*—Medium.
- *Surface.*—Smooth to medium rough.
- *Lenticels.*—Numerous. Medium size.
- *Color.*—Reddish brown to brown.

Leaves:
- *Size.*—Large. Average length — $5\frac{1}{4}$ to $5\frac{7}{8}$". Average width — $2\frac{1}{2}$ to 3".
- *Shape.*—Ovate to orbicular.
- *Texture.*—Smooth.
- *Margin.*—Serrate.
- *Petiole.*—Size — large. Average length — $1\frac{3}{4}$". Average width — 1/16.
- *Glands.*—Size — small. Globose. Number varies from 0–4. Average number 2. Located on upper portion of petiole and lower portion of leaf blade.

*Color.*—Upper surface — green to dark green (27-E-7) to (27-F-7). Lower surface — green to grayish green (27-D-4) to (27-D-6).

Flower buds:

*Size.*—Medium.

*Length.*—Medium.

*Shape.*—Plump.

Flowers:

*Blooming period.*—Feb. 21, 1990 to Feb. 27, 1990. Varies with climatic conditions.

*Size.*—Large.

*Color.*—Pink — fades to nearly white at petal fall.

*Pistil.*—Pubescent.

*Pollen.*—Present.

Fruit:

*Maturity when described.*—Firm ripe.

*Date of first picking.*—May 19, 1990.

*Date of last picking.*—May 24, 1990.

*Size.*—Large. Average diameter axially — 2" to 2¼". Average transversely in suture plane — 2" to 2¼". Average diameter measured at right angles to suture plane — 2" to 2¼".

*Form.*—Nearly globose, slightly larger on one side, flattened at base.

*Suture.*—Usually pronounced extends from base to apex.

*Ventral surface.*—Nearly rounded, slightly lipped at stem end.

*Cavity.*—Rounded to slightly elongated in suture plane. Average depth — ¼". Average breadth — ⅜".

*Base.*—Retuse, slightly more flattened on the side opposite the suture.

*Apex.*—Rounded to slight depression, usually on side opposite the suture.

Skin:

*Thickness.*—Medium.

*Texture.*—Medium — tenacious to flesh.

*Down.*—Scant, very short.

*Tendency to crack.*—Very little.

*Color.*—Apricot yellow to yellowish orange (6-A-4) to (6-A-7). Slight reddish orange blush (7-A-5) to (7-A-6) on fruit exposed to sun.

Flesh:

*Ripens.*—Evenly.

*Texture.*—Firm.

*Fiber.*—Few, small, tender.

*Aroma.*—Pronounced.

*Flavor.*—Good, mild, subacid.

*Eating quality.*—Good.

*Juice.*—Moderate.

*Color.*—Golden yellow to light orange (6-A-5) to (6-A-7).

Stone:

*Type.*—Freestone.

*Size.*—Medium. Average length — 1⅛". Average width — 1". Average thickness —½".

*Form.*—Ovoid.

*Base.*—Varies from straight to rounded.

*Apex.*—Varies from rounded to slight point.

*Sides.*—Equal to unequal.

*Surface.*—Pitted throughout, slightly deeper toward side.

*Ridges.*—Two distinct ridges across surface on opposite sides of suture plane.

*Tendency to split.*—None.

*Color.*—Brown to light brown (6-C-6) to (6-D-5).

Use: Dessert.

*Market.*—Local and long distance.

Keeping quality: Good.

Shipping quality: Good.

The new apricot tree, its flowers, foliage and fruit herein described may vary in slight detail due to climatic, soil conditions and cultural practices under which the variety may be grown; the present description is that of the variety grown under the ecological conditions prevailing near Modesto, Calif.

We claim:

1. A new and distinct variety of apricot tree, substantially as illustrated and described, which is of large size, vigorous, semi-spreading in growth and a productive and regular bearer of large, firm, yellow flesh, freestone fruit with good flavor and eating quality and the ability to ship to long distance markets; the new variety is further characterized when compared to Flaming Gold Apricot (U.S. Plant Pat. No. 2,822) as having greater production and being approximately 12 days earlier in maturity.

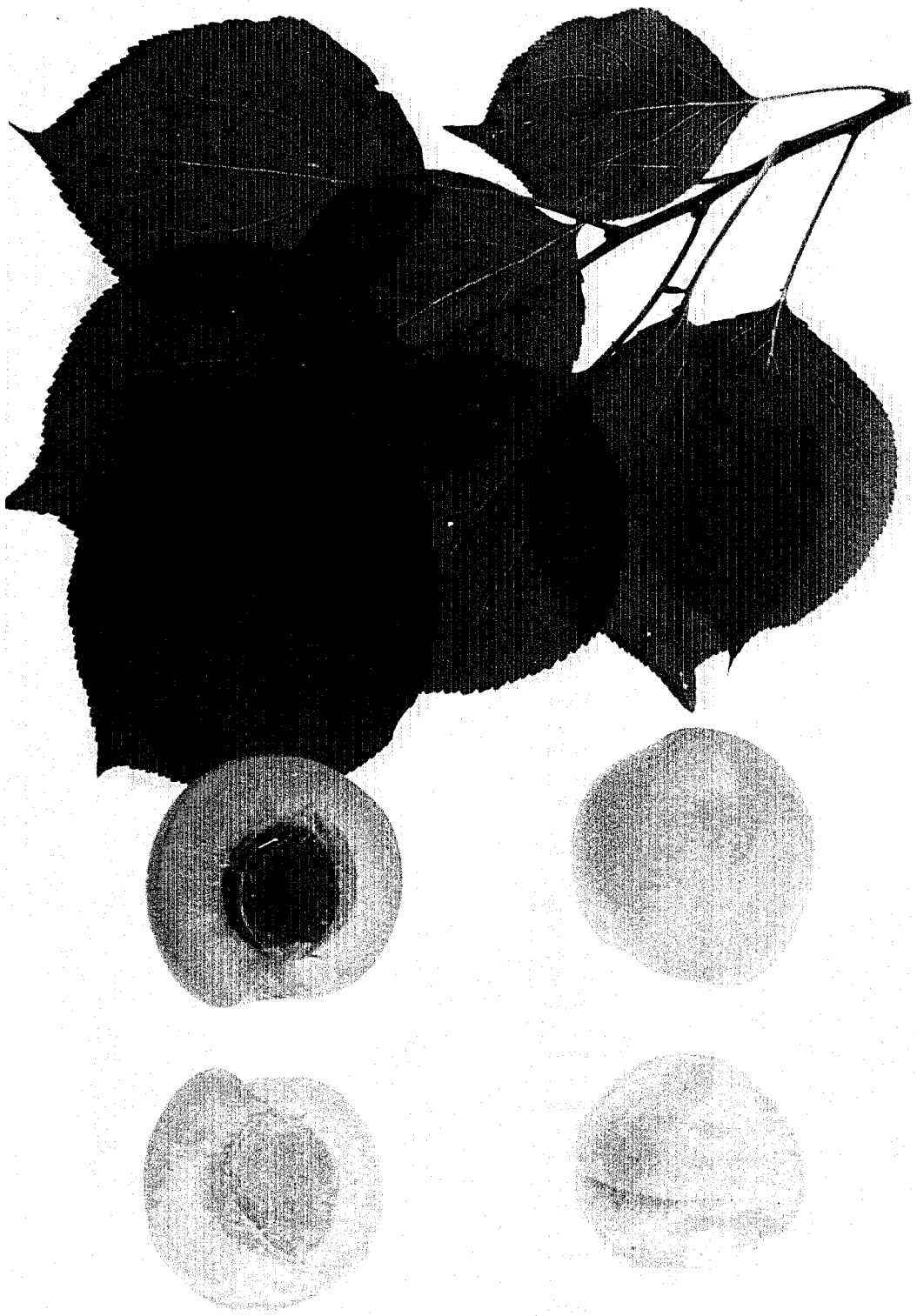

* * * * *